United States Patent [19]
Posluszny

[11] Patent Number: 5,287,117
[45] Date of Patent: Feb. 15, 1994

[54] COMMUNICATION SYSTEM FOR TRANSMITTING DATA BETWEEN A TRANSMITTING ANTENNA UTILIZING A PHASED ARRAY ANTENNA AND A RECEIVE ANTENNA IN RELATIVE MOVEMENT TO ONE ANOTHER

[75] Inventor: Jerry C. Posluszny, Stickney, Ill.

[73] Assignee: Kabushiki Kaisha Toshiba, Kanagawa, Japan

[21] Appl. No.: 933,907

[22] Filed: Aug. 27, 1992

Related U.S. Application Data

[63] Continuation of Ser. No. 426,743, Oct. 26, 1989, abandoned.

[51] Int. Cl.5 .................. H01Q 1/44; H01Q 21/20; A61B 6/03
[52] U.S. Cl. .................. 343/763; 343/799; 378/4; 378/15
[58] Field of Search .............. 343/799, 800, 763, 816, 343/757, 853, 795; 378/4, 15; 342/398, 399, 403–406, 430; 455/39–41, 80, 81, 132–136, 327, 333; H01Q 21/20, 9/28, 1/44, 3/00

[56] References Cited

U.S. PATENT DOCUMENTS

| | | | |
|---|---|---|---|
| 2,461,187 | 2/1949 | Steinmann | 342/398 |
| 2,717,379 | 9/1955 | Earp | 342/404 |
| 3,432,657 | 3/1969 | Slavin | 378/15 |
| 3,747,114 | 7/1973 | Shyhalla | 343/795 |
| 3,936,835 | 2/1976 | Phelan | 343/840 |
| 4,103,304 | 7/1978 | Burnham et al. | 343/853 |
| 4,427,983 | 1/1984 | Kruger | 343/763 |
| 4,538,125 | 8/1985 | Beckmann et al. | 378/15 |
| 4,555,708 | 11/1985 | Waineo et al. | 343/799 |
| 4,796,183 | 1/1989 | Ermert et al. | 378/15 |
| 5,140,696 | 8/1992 | Fox | 378/15 |
| 5,157,393 | 10/1992 | Fox et al. | 378/15 |

Primary Examiner—Rolf Hille
Assistant Examiner—Peter Toby Brown
Attorney, Agent, or Firm—Finnegan, Henderson, Farabow, Garrett & Dunner

[57] ABSTRACT

A communication system for transmitting data between a transmitting platform and a receiving platform moving relative to each other. A phased array antenna forms the transmitting antenna rotated on the transmitting platform and a single dipole, oriented parallel to the transmitting antenna, forms the receive antenna located on the receiving platform. The phased array antenna is split into small sections, each section comprising dipole elements and a matching network, including a feedpoint. The receive antenna is mounted close to the transmitting antenna.

13 Claims, 2 Drawing Sheets

COMMUNICATION SYSTEM FOR TRANSMITTING DATA BETWEEN A TRANSMITTING ANTENNA UTILIZING A PHASED ARRAY ANTENNA AND A RECEIVE ANTENNA IN RELATIVE MOVEMENT TO ONE ANOTHER

This application is a continuation of application Ser. No. 07/426,743 filed Oct. 26, 1989, now abandoned.

BACKGROUND OF THE INVENTION

The present invention relates to a communication system and, more particularly, to a system for transmitting data between a transmitting platform and a receiving platform using a phased array antenna as the transmitting antenna located on the transmitting platform.

For cross-reference purposes, the existence of two filed applications are noted. The first application is Ser. No. 07/316,991, which ultimately became U.S. Pat. No. 5,157,393, entitled "Communication System for Transmitting Data Between a Transmitting Antenna Utilizing Leaky Coaxial Cable and a Receive Antenna in Relative Movement to One Another," by Timothy R. Fox and Jerry C. Posluszny. The second application is Ser. No. 07/317,026, now U.S. Pat. No. 5,140,696, entitled "Communication System for Transmitting Data Between A Transmitting Antenna Utilizing Strip-Line Transmission Line and a Receive Antenna in Relative Movement to One Another," by Timothy R. Fox. These applications and the present application are commonly owned by the same Assignee.

A communication system for transmitting data between a rotating platform and a stationary platform finds particular utility in CT scanners. The data come from a transmitter source and are applied to a suitable modulator that modulates a sinusoidal radio-frequency carrier signal. The modulated carrier signal is applied to the feedpoint of the transmitting antenna. The transmitter carrier source, the suitable modulator and the transmitting antenna are mounted on the transmitting platform, and the transmitting platform is rotating.

The transmission often is achieved using brushes sliding against slip rings to make a set of electrical connections between the rotating and stationary platforms. This mechanical contact causes a number of problems, however. One problem is that the mechanical interface is highly susceptible to wear. A second problem is that the mechanical interface achieves only an intermittent electrical contact.

Another problem with present CT scanners is that a large portion of the equipment rotates, but the data received from the rotating equipment must be communicated to a computer that does not rotate. Aside from the mechanical linkages discussed above, other CT scanners use flexible cables to connect the rotating platform to the fixed platform. As a result, most present CT scanners cannot allow the platform to rotate continuously. Thus, the rotating platform will make, for example, two rotations and then the transmitting cable must be rewound and the rotation started over again for another two rotations. This procedure causes wear on, and early destruction of the cables. Moreover, the scanning procedure is rendered unnecessarily long because the platform cannot continuously rotate.

SUMMARY OF THE INVENTION

Accordingly, it is an object of the invention to provide a communication system for transmitting data between a transmitting platform and a receiving platform that eliminates the mechanical interface and the wear of mechanical apparatus as the receive antenna located on the receiving platform moves along the transmitting antenna located on the transmitting platform.

It is another object of the present invention to provide a communication system for transmitting data between a transmitting platform and a receiving platform that has continuous electrical contact as the receive antenna located on the receiving platform moves along the transmitting antenna located on the transmitting platform.

It is a further object of the present invention to permit continuous relative rotation between the transmitting platform and the receiving platform, thereby increasing the life of the transmitting antenna and decreasing the time necessary to complete a CT scan procedure.

The objects given above are accomplished, in part, using a phased array antenna as the transmitting antenna and by forming the transmitting antenna into a circle. Additional objects and advantages of the present invention will be set forth in part in the description that follows and in part will be obvious from the description or may be learned by practice of the invention. The objects and advantages of the invention may be realized and obtained by the methods and apparatus particularly pointed out in the appended claims.

To achieve the objects and in accordance with the purpose of the invention, as embodied and as broadly described herein, a communication system for transmitting data between a transmitting platform and a receiving platform, the transmitting and receiving platforms moving relative to each other, comprises a transmitting antenna located on the transmitting platform, the transmitting antenna being a phased array antenna, the phased array antenna disposed to form a circle, driving means for inputting the data to the transmitting antenna, a receive antenna located on the receiving platform, the receive antenna being maintained a first predetermined distance from the transmitting antenna, and receiving means for receiving the data from the receive antenna.

The accompanying drawings, which are incorporated in and constitute a part of the specification, illustrate the invention and, together with the description, serve to explain the principles of the invention.

DESCRIPTION OF THE PREFERRED EMBODIMENT

Figure 1:
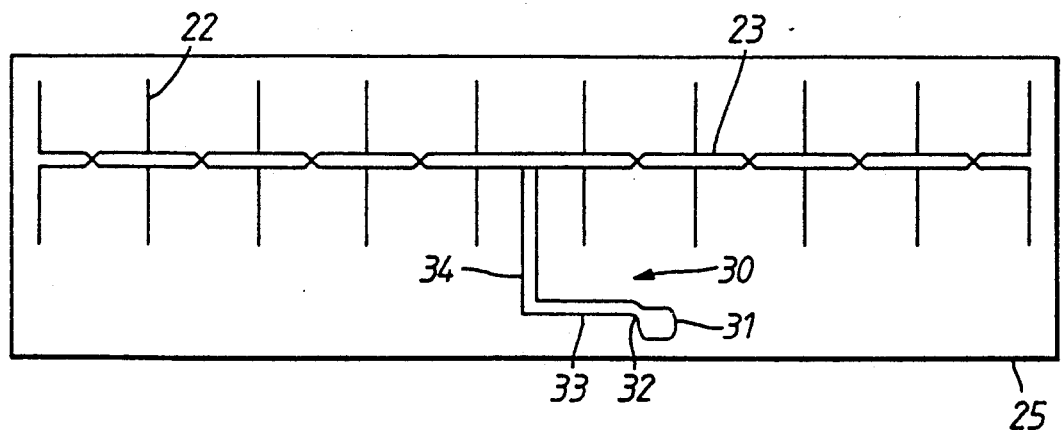
FIG. 1 is a functional block diagram depicting the phased array antenna utilized as the transmitting antenna in the preferred embodiment of the communication system.

Reference will now be made in detail to the presently preferred embodiment of the invention, an example of which is illustrated in the accompanying drawings. Throughout the drawings, like reference characters are used to indicate like elements.

Figure 2:
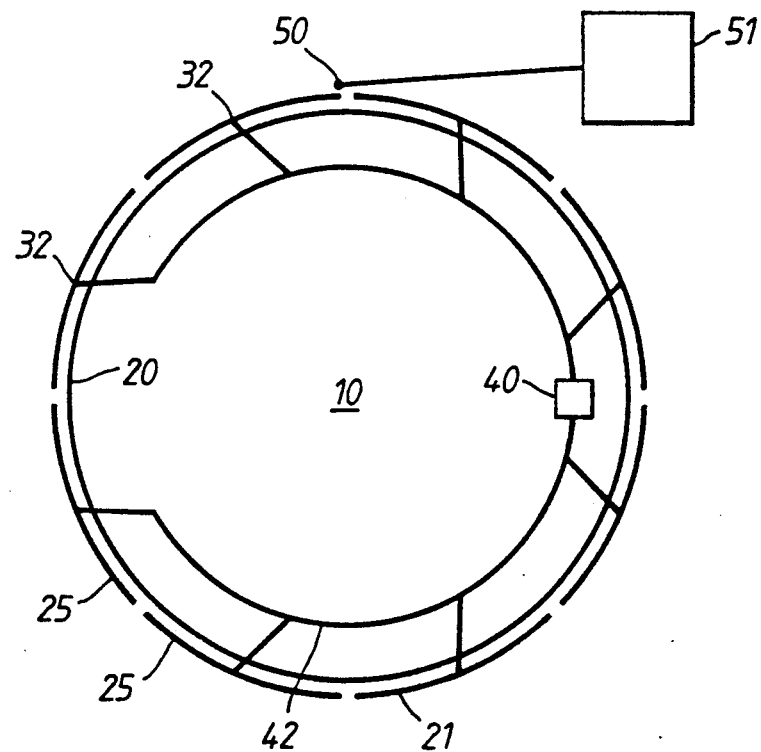
FIG. 2 is a functional block diagram depicting a preferred embodiment of the communication system for transmitting data between a transmitting platform and a receiving platform wherein the transmitting antenna located on the transmitting platform is a phased array antenna.

A preferred embodiment of the communication system according to the present invention is shown in FIG. 2 and is generally designated by reference character 100. As explained further herein below, system 100 is a communication system for transmitting data between a transmitting platform and a receiving platform in relative movement to one another.

According to the present invention, a transmitting antenna 10 is provided, located on a transmitting platform 20 having a phased array antenna 21. As embodied herein, transmitting platform 20 has a top surface made of a suitable dielectric material and a bottom surface made of a solid sheet of copper (not shown). According to the presently preferred embodiment, transmitting platform 20 is either an annular disc or a drum. Other structures are considered to be apparent to those skilled in the art and are considered within the scope of the invention.

Phased array antenna 21 is split into small sections 25. One section 25 is illustrated in FIG. 1. Each section 25 comprises dipole elements 22 that are one-half the electrical wavelength of the frequency used, and are spaced apart one-half the electrical wavelength of the frequency used. Dipole elements 22 are connected to each other within each section 25 by transmission line 23, forming a colinear array.

Each section 25 also includes a matching network 30. Matching network comprises a transmission line balun 31, a coaxial feedpoint 32, transmission line transformers 33, and matching transmission lines 34. Coaxial feedpoint 32 is used for inputting data, and the impedance seen at coaxial feedpoint 32 preferably is 50 ohms. Matching transmission line 34 is one-half the electrical wavelength of the frequency used.

Referring again to FIG. 2, according to the present invention, phased array antenna 21 can comprise, for example, eight sections 25 that are mounted radially around the circumference of transmitting platform 20. Other even numbers of sections 25 may be used as phased array antenna 21, and are considered to be apparent to those skilled in the art and are considered within the scope of the invention. Also, the phased array antenna may be disposed on the flat surface of transmitting platform 20. Other structures are considered apparent to those skilled in the art and are considered to be within the scope of the invention.

According to the present invention, a driving means is provided for inputting data to transmitting antenna 10 at feedpoints 32. As embodied herein, the driving means is designated by reference character 40 and may include a power splitter. The power splitter of driving means 40 can be mounted a distance of approximately four (4) meters from feedpoint 32 and can be connected to feedpoint 32 of each section 25 with matched-length normal coaxial cables 42 of the same characteristic impedance. Other distances between the power splitter and the feedpoints can be used and are considered within the scope of the invention. The power splitter includes a resistor network, a transformer-coupled hybrid network or a transmission line network (not shown). Such networks permit tight controls on the phase shift and equality of power splitting between the outputs of the power splitter. If the outputs from the power splitter are terminated with the correct impedance, the voltage across the load impedances will be equal and in phase. Such networks are well known in the art and need not be described for purposes of the present invention.

The present invention further provides a receive antenna. As embodied herein, the receive antenna is designated by reference character 50. Receive antenna 50 is a single dipole, one-half the electrical wavelength of the frequency used. The dipole is oriented parallel to transmitting antenna 10.

The present invention further provides a receiving means for receiving data from receive antenna 50. As embodied herein, the receiving means is designated by reference character 51. Receiving means 51 includes an amplifier or a receiver, a suitable filter, and a detector for the frequency and modulation employed. According to the presently preferred embodiment, the first amplifier of receiving means 51 is located on the receiving platform approximately less than ten (10) centimeters from receive antenna 50. Other distances between the first amplifier of receiving means 51 and receive antenna may be employed, however, and are considered within the scope of the invention.

The present invention also provides that receive antenna 50 be maintained approximately 1 to 2 (1-2) millimeters from transmitting antenna 10. Other distances between receive antenna 50 and transmitting antenna 10 that will ensure that receive antenna 50 is in the near field of transmitting antenna 10 may be used and are considered within the scope of the invention. At matching network 30 of each section 25, receive antenna 50 is disposed to clear the connection of matching network 30 without causing large changes in the spacing between transmitting antenna 10 and receive antenna 50.

Operation of the invention will now be explained with reference to the preferred embodiment illustrated in FIG. 2. The presently preferred operation provides that data are input to transmitting antenna 10 via the power splitter of driving means 40. The data input to feedpoints 32 on each section 25 of phased array antenna 21 are equal signals, in phase from a common source, and include a serial stream with binary values encoded to include error correction capability. A suitable sinusoidal voltage generator makes a "carrier" voltage, and this carrier voltage turns on and off in response to the binary value of the data stream. At receive antenna 50, the output signal is amplified to a voltage level high enough to allow an amplitude detector to demodulate the signal at receiving means 51. The demodulated signal is then applied to a voltage comparator to discriminate between carrier-on and carrier-off conditions.

An alternative operation of the device is to apply input data of a serial stream of binary values to a frequency modulator. A frequency modulator makes a "mark" and "space" frequency in response to the binary value of the data stream. The output signal is demodulated by a suitable frequency demodulator at receiving means 51. The demodulated signal is then discriminated between the mark and space frequency.

Other arrangements for developing the data signals are considered to be within the scope of the invention and are considered to be apparent to those skilled in the art.

If the system is unstable, or if the operating frequency is changed often, a superheterodyne system may be used with either the amplitude modulation or the frequency modulation receive antenna 50 and the antenna signal is converted to an intermediate frequency for convenience detection.

If there is excessive interference on the receive antenna from outside sources or if the transmitting antenna produces excessive interference to outside devices, the entire system, i.e., the transmitting antenna and receive antenna, may be enclosed inside a suitable metal shield. According to the presently preferred embodiment, the metal shield is an annular box with a rectangular cross-section cut into two parts. One part shields the transmitting platform, the other shields the receiving platform. The two sections of metal shields are rotating in relation to each other. Other structures are considered to be apparent to those skilled in the art in view of this disclosure and are considered within the scope of the invention.

Figure 3:
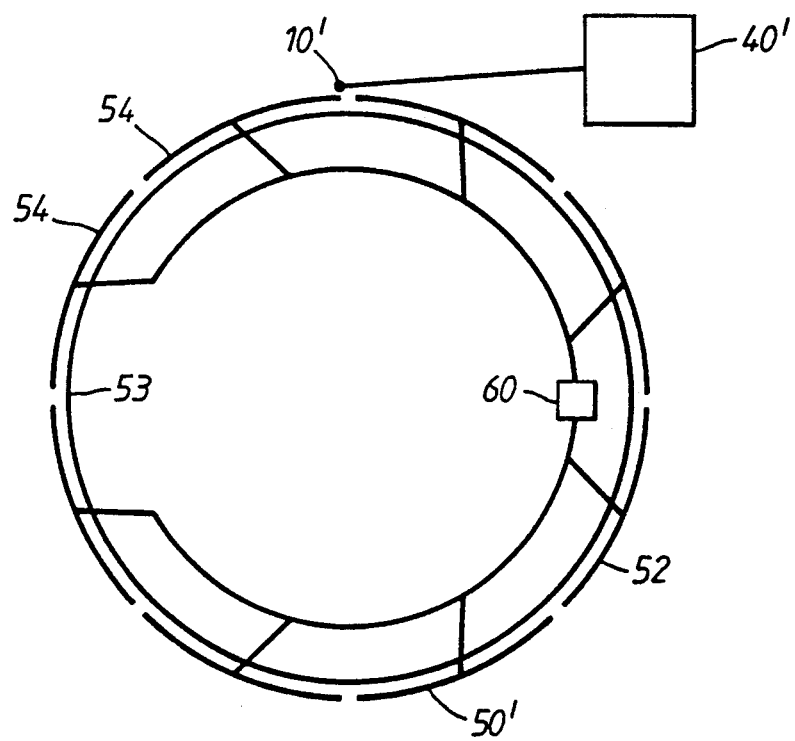
FIG. 3 is a functional block diagram depicting a second embodiment of a communication system for transmitting data between a transmitting platform and a receiving platform wherein the receiving antenna is a phased array antenna.

A further embodiment of the communication system according to the present invention will now be discussed with respect to FIG. 3. This embodiment differs from the preferred embodiment in that the transmitting antenna and the receive antenna are reversed. Turning to the embodiment of a communication system according to the present invention illustrated in FIG. 3, it is seen that transmitting antenna 10' is a single dipole, one-half the electrical wavelength of the frequency used. Driving means 40' is provided for inputting data to transmitting antenna 10'. Receive antenna 50' is a phased array antenna 52, located on a receiving platform 53. Receiving platform 53 has a top surface made of a suitable dielectric material and a bottom surface made of a solid sheet of copper (not shown). According to the second embodiment, receiving platform 53 is either an annular disc or drum. Other structures are considered to be apparent to those skilled in the art and are considered within the scope of the invention.

Phased array antenna 52 is split into small sections 54. Each section 54 comprises dipole elements that are one-half the electrical wavelength of the frequency used, and are spaced apart one-half the electrical wavelength of the frequency used (not shown). Phased array antenna 52 can comprise, for example, eight sections 54 that are mounted radially around the circumference of receiving platform 53. The second embodiment of the present invention further provides a receiving means for receiving data from receive antenna 50'. As embodied herein, the receiving means is designated by reference character 60.

The present invention may, therefore, be summarized as providing a communication system for transmitting data between a transmitting platform and a receiving platform using a phased array antenna as the transmitting antenna located on the transmitting platform wherein there is no mechanical interface and wear on mechanical apparatus, and there is continuous electrical contact as the receive antenna slides along the transmitting antenna. Furthermore, the present invention allows continuous relative rotation between the transmitting and receiving platforms thereby increasing the life of the transmitting antenna and decreasing the time necessary to complete a CT scan procedure, for example.

It will be apparent to those skilled in the art that modifications and variations can be made in the communication system of the present invention. The invention in its broader aspects is, therefore, not limited to the specific details, representative methods and apparatus, and illustrated examples shown and described herein. Thus, it is intended that all matter contained in the foregoing description and shown in the accompanying drawings, shall be interpreted as illustrative and not in a limiting sense.

What is claimed is:

1. A communication system for transmitting data between a transmitting platform and a receiving platform, the transmitting platform being maintained a first predetermined distance from the receiving platform, the transmitting and receiving platforms moving relative to each other, comprising:
   a transmitting antenna located on the transmitting platform, the transmitting antenna being split into a number of small sections comprising a number of dipole elements and a matching network, the dipole elements in each small section being spaced apart one-half of an electrical wavelength of a frequency used by the communication system, the small sections being disposed to form a circle;
   driving means for inputting the data in phase from a common source to each small section of the transmitting antenna;
   a receive antenna located on the receiving platform; and
   receiving means for receiving data from the receive antenna and for demodulating the received data.

2. The communication system as recited in claim 1, wherein the number of small sections is 8.

3. The communication system as recited in claim 1, wherein the number of dipole elements is 10.

4. The communication system as recited in claim 1, wherein the matching network comprises a transmission balun, a coaxial feedpoint, a transmission line transformer, and a matching transmission line.

5. The communication system as recited in claim 1, wherein the driving means includes a power splitter.

6. The communication system as recited in claim 1, wherein the receiving means is a single dipole element.

7. The communication system as recited in claim 1, wherein the receiving means is maintained a second predetermined distance from the receive antenna.

8. A communication system for transmitting data between a transmitting platform and a receiving platform, the transmitting platform being maintained a first predetermined distance from the receiving platform, the transmitting and receiving platforms moving relative to each other, comprising:
   a transmitting antenna located on the transmitting platform;
   driving means for inputting the data in phase from a common source to the transmitting antenna;
   a receive antenna located on the receiving platform, the receive antenna being split into a number of small sections comprising a number of dipole elements and a matching network, the dipole elements in each small section being spaced apart one-half of an electrical wavelength of a frequency used by the communication system, the small sections being disposed to form a circle; and
   receiving means for receiving the data from the receive antenna and for demodulating the received data.

9. The communication system as recited in claim 8, wherein the number of small sections is 8.

10. The communication system as recited in claim 8, wherein the number of dipole elements is 10.

11. The communication system as recited in claim 8, wherein the matching network comprises a transmission balun, a coaxial feedpoint, a transmission line transformer, and a matching transmission line.

12. The communication system as recited in claim 8, wherein the transmitting antenna is a single dipole element.

13. The communication system as recited in claim 8, wherein the receiving means is maintained a second predetermined distance from the receive antenna.

* * * * *